United States Patent [19]

Mooradian et al.

[11] Patent Number: 5,782,770

[45] Date of Patent: Jul. 21, 1998

[54] HYPERSPECTRAL IMAGING METHODS AND APPARATUS FOR NON-INVASIVE DIAGNOSIS OF TISSUE FOR CANCER

[75] Inventors: Greg Mooradian, Mililani, Hi.; Mark Weiderhold, San Diego, Calif.; Ali E. Dabiri, San Diego, Calif.; Chris Coyle, San Diego, Calif.

[73] Assignee: Science Applications International Corporation, San Diego, Calif.

[21] Appl. No.: 924,912

[22] Filed: Sep. 8, 1997

Related U.S. Application Data

[63] Continuation-in-part of Ser. No. 241,992, May 12, 1994, abandoned.

[51] Int. Cl.$^6$ .................................................. A61B 6/00
[52] U.S. Cl. ................................................ 600/476
[58] Field of Search ............................. 600/407, 473, 600/476, 310; 356/303, 341, 379, 432, 408, 448, 318, 328; 250/574, 358.1, 339.01, 339.09; 348/269, 207

[56] References Cited

U.S. PATENT DOCUMENTS

| | | | |
|---|---|---|---|
| 4,170,987 | 10/1979 | Anselmo et al. | 128/665 |
| 4,515,165 | 5/1985 | Carroll | 128/664 |
| 4,556,057 | 12/1985 | Hiruma et al. | 128/303.1 |
| 4,948,974 | 8/1990 | Nelson et al. | 128/664 |
| 4,975,581 | 12/1990 | Robinson et al. | 128/633 |
| 5,078,150 | 1/1992 | Hara et al. | 128/665 |
| 5,088,493 | 2/1992 | Giannini et al. | 128/633 |
| 5,303,026 | 4/1994 | Strobl et al. | 128/665 |
| 5,305,759 | 4/1994 | Kaneko et al. | 128/665 |
| 5,318,024 | 6/1994 | Kittrell et al. | 128/665 |
| 5,507,287 | 4/1996 | Palcic et al. | 128/665 |

OTHER PUBLICATIONS

Cothren et al, "Gastrointestinal tissue diagnosis . . .", 1990 vol. 36 No. 2 Gastrointestinal Endoscopy.

Anderson et al, "Autofluorescence of Various Rodent . . ." 1986, Lasers in Medical Science vol. 2:41.

Anderson–Engels et al, "Multicolor fluorescence imaging system . . .", 1990 SPIE vol. 1205 Bioimaging/Spectroscopy.

Marchesini et al, "In vivo Spectrophotometric . . ." 1992, Photochemistry and Photobiology vol. 55 No. 4.

*Primary Examiner*—Brian Casler
*Attorney, Agent, or Firm*—Page Lohr Associates

[57] ABSTRACT

Techniques and devices for diagnosing tissue via hyperspectral imaging are presented. A three dimensional "image" where one dimension contains spectral information is formed from a region of interest. The spectral content of the image can be analyzed on a pixel-by-pixel basis to determine the presence of certain matter and the spatial extend thereof. The techniques are non-invasive and do not require introduction of agents typically required to facilitate interaction with illumination sources.

5 Claims, 7 Drawing Sheets

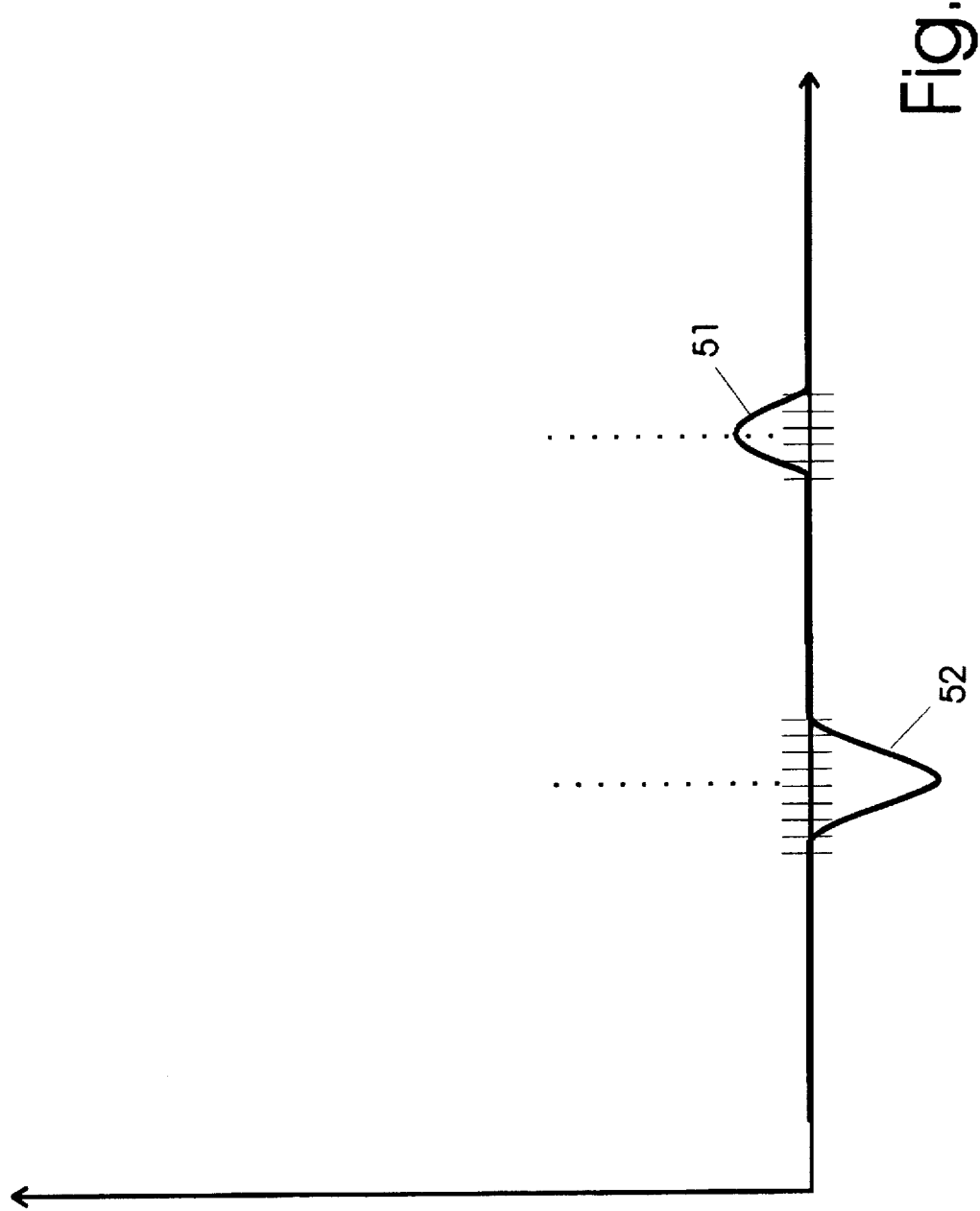

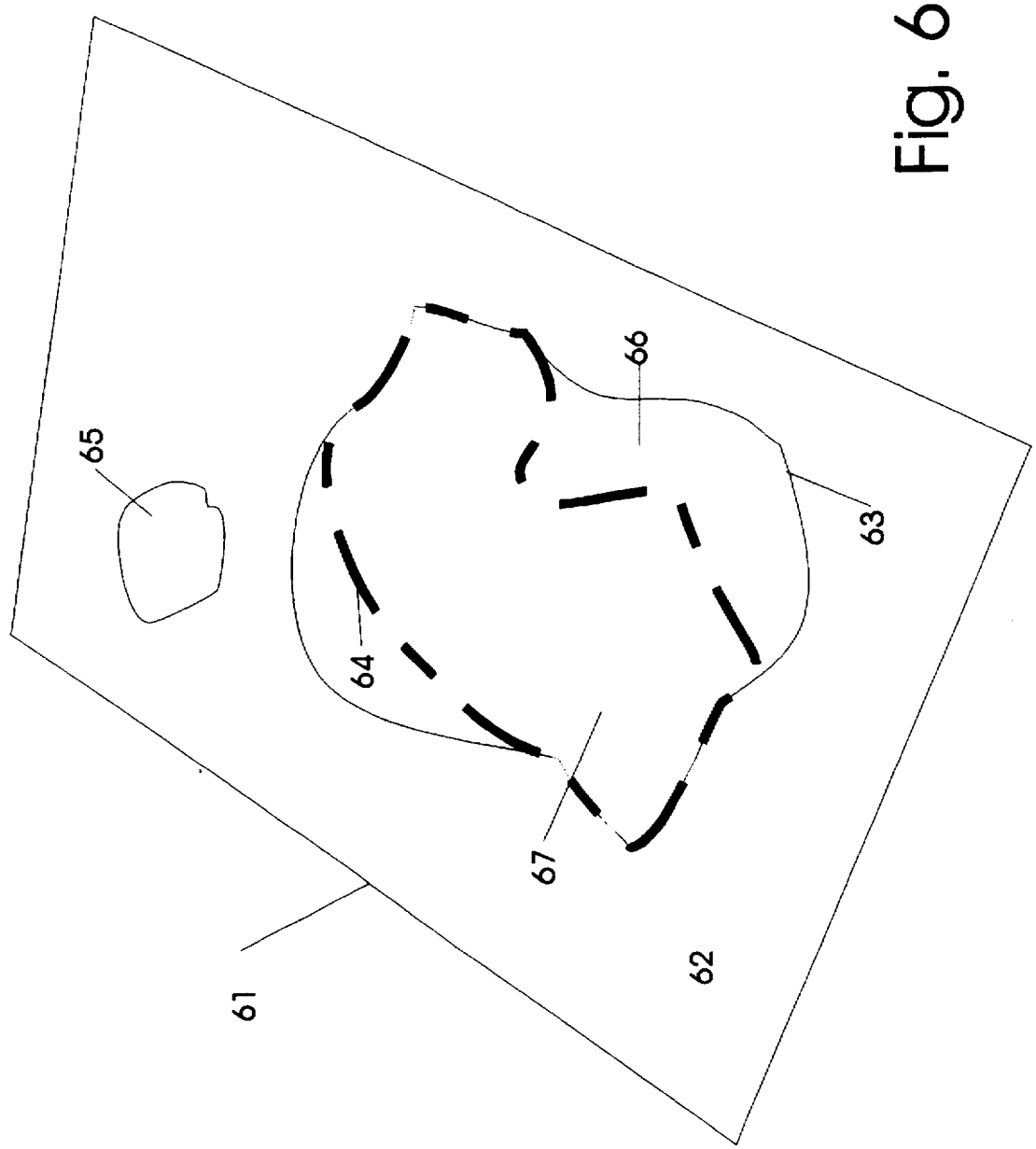

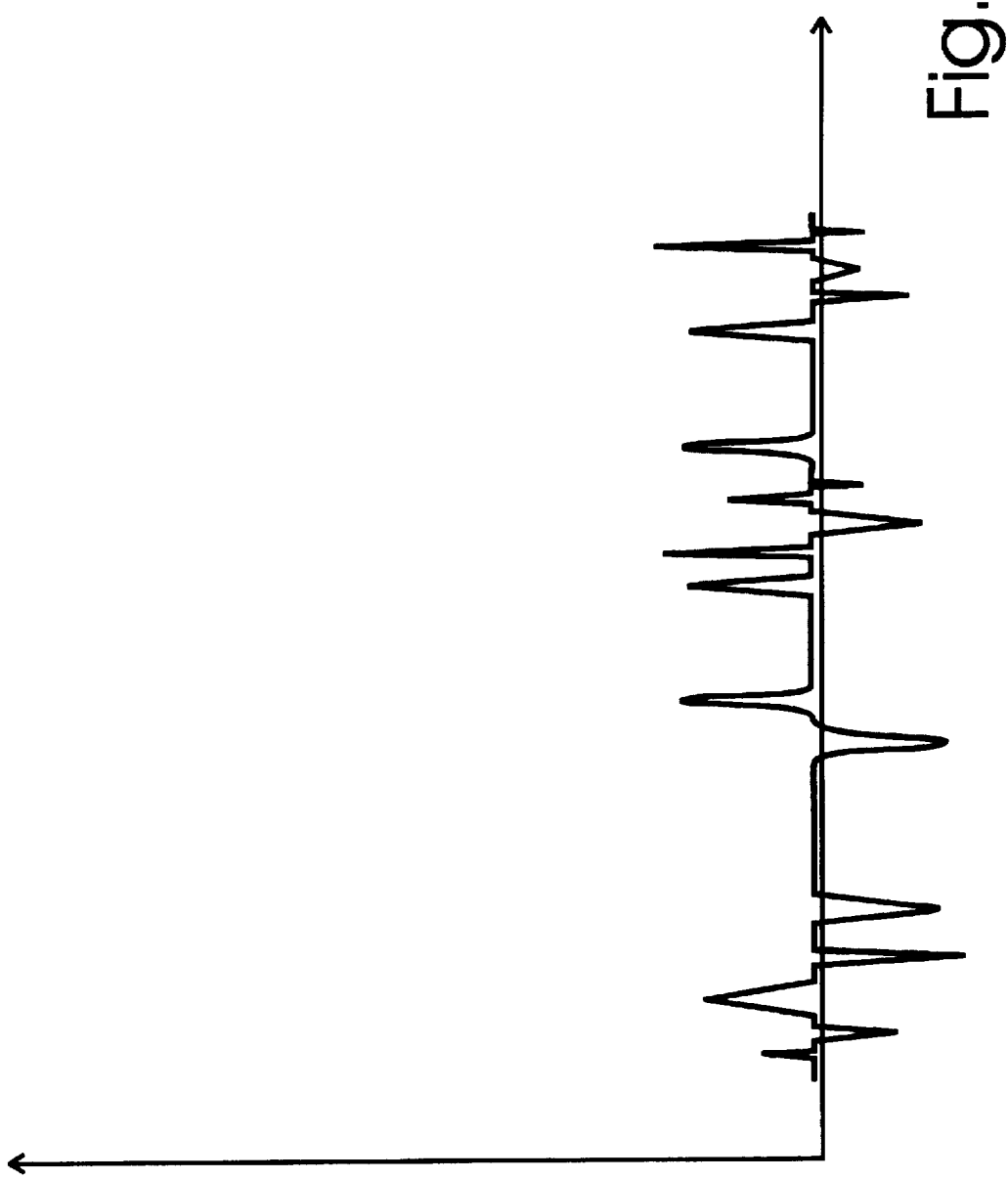

HYPERSPECTRAL IMAGING METHODS AND APPARATUS FOR NON-INVASIVE DIAGNOSIS OF TISSUE FOR CANCER

BACKGROUND OF THE INVENTION

This application is a continuation-in-part application of a previously filed application having a Ser. No. of 08/241,992 filed May 12, 1994, now abandoned. The entire text of that application is incorporated herein by reference. This invention is generally concerned with hyperspectral imaging of tissue and specifically concerned with hyperspectral imaging as it relates to the diagnosis of cancerous tissues.

Although imaging systems are generally concerned with spatial properties of an object field, some imaging systems may also be concerned with spectral properties of an object field. Imaging usually refers to the representation of an object field by a spatially varying pattern. The intensity of light which emanates from an object can be detected by an imaging system and used to form a pattern on some medium. Although spatial patterns yield certain information about an object field, spectral or color features of the object field may also be of interest. Image detectors such as CCD cameras use silicon devices to measure the intensity and color of light from an object field. From these measurements an image having a spatially varying pattern of colors can be formed.

An image can be thought of as a two dimensional array of spatially resolved elements sometimes called "pixels". A pixel is the spatial resolution unit. An image pixel can represent an intensity value for monochrome (grayscale) images and a color and intensity level for color images. The true color of an object field pixel can be represented in an image via various combinations of three primary colors generated in the image medium. Color cathode ray tube images and color photographic images usually approximate color this way. Color presented as such is only an approximation of the true color of an object field element.

When the spectral properties of an object field are of particular interest, it may not be sufficient to represent color in the way that simple imaging systems do. An accurate measurement of each of a plurality of color bands may be necessary. Imaging systems having both high spatial resolution and high chromatic or spectral resolution are sometimes called hyperspectral imaging systems. This is distinguished from multicolor imaging system which typically have broadband properties (i.e. several 10s of nanometers in bandwidth). A hyperspectral image typically has bandwidth channels less than 10 nanometers wide. Hyperspectral imaging systems have spatial resolution elements as well spectral resolution elements. A hyperspectral image can be thought of as a three dimensional image where two of the dimensions are spatial and one dimension is spectral.

Hyperspectral imaging techniques may be found in science fields such as remote sensing and Earth observation where systems have been developed for various objectives. Of these, we find devices flown on satellites and airplanes to "look" at terrain or oceans having interesting spectral features. These include but are not limited to "Landsat 1"; Geophysical Environmental Research, (GER); a NASA Airborne Visible Infrared Imaging Spectrometer, (AVIRIS); and others.

Examples of multicolor imaging systems which concern themselves with certain object spectral properties can be found in many other fields. For example, in the medical field we can find use of spectrally resolved images to learn details of object characteristics which relate to color.

Anselmo et al disclose an invention in U.S. Pat. No. 4,170,987 which is related to a "Medical Diagnosis System and Method with Multispectral Imaging". The importance of multispectral images as they relate to physiological effects is well illustrated in the disclosure of Anselmo et al. In particular, the degree of burns is related to the transmission of certain wavelengths of light in tissue. By employing an intensity subtraction scheme between various chromatic signals with respect to electronic images, see column 3, lines 39–57, intensity ratios are used for diagnosis of tissue burns. Three separate light filters, IR, red and green, are employed (abstract) to analyze each pixel element of the area of interest. Because the three spectral regions interact differently with tissue being addressed, the system can be used to derive information for use in a diagnosis. We call an imaging system which separates light into a few broad spectral bands a "multispectral imaging" system.

The invention of Carroll discloses in U.S. Pat. No. 4,515,165 a method to detecting tumors in animals and humans. A shadowgraph image is made using either a single wavelength gray scale or false color imaging techniques. The degree of absorption and scattering of light depends on the functional state of the tissue being examined. Carroll teaches in the summary "because visible and infrared radiation absorption characteristics are quite different in oxygenated and reduced blood, one can readily produce images with such radiation which readily differentiate between oxygenated blood and deoxygenated blood containing tissue". Again, broad spectrum interactions with tissue mechanisms can yield information relating to the state of tissues.

Hiruma et al teach in U.S. Pat. No. 4,556,057 a cancer diagnosis device which contains a plurality of laser beams. The laser beams excite a fluorescence which responds differently to various tissue states. The emission of fluorescence is a broadband spectral phenomena. Intensity "peaks" associated with known interactions can be singled out with spectral filters tuned to those spectral regions of interest. Hiruma sets forth some of these interactions and ways which they relate to early detection of cancer.

There are other similar inventions relating to laser induced fluorescence used for cancer tumor detection. In a paper published by Anderson et al in the IEEE journal of Quantum Electronics, Vol. QE-23, No 10 in October 1987 one such method is described. Similar techniques are also found in a paper by Cothern et al in Gastrointestinal Endoscopy, Volume 36, No. 2 1990. Each of these describe techniques which employ a look at certain broadband spectral features. Spectral features which are the result of some known interaction of light and a property of the tissue of interest. Passband filters used at a detector input are tuned to those spectral regions of interest. Sometimes an agent is introduced to be absorbed by a particular tissue where the agent responds to a laser induced fluorescence scheme. These agents have strong optical responses which are easy to detect with multicolor imaging systems. However, it is undesirable to have the requirement of introducing some agents into healthy tissue. In addition, there is generally a time requirement for the agent to be absorbed by the tissue. These problems and others strongly suggest a need to obviate the use of agents to detect cancer.

Notwithstanding, systems and techniques have now been discovered which provide novel uses of hyperspectral imaging; uses which relate particularly to the diagnosis of tissue as it relates to detection and analysis of cancers. In contrast to the good and useful inventions mentioned herein, each having certain features that are no less than remarkable, the instant invention is concerned with deriving information from a plurality of chromatically resolved images, or hyperspectral images, for the diagnosis of tissue. While previous methods were concerned with particular broad band spectral features, the present invention is concerned with narrow band spectral features. By considering highly resolved spectral signatures, one enables new techniques of data handling which may yield accurate diagnosis of tissue. Further, the techniques may eliminate the need for secondary invasive procedures used to enable old methods.

SUMMARY OF THE INVENTION

The present invention employs non-evasive hyperspectral imaging systems and techniques to diagnose tissue for the purpose of detecting the presence of cancer. The invention is distinguished from similar techniques in that a hyperspectral image contains detailed spectral information which can be analyzed for spectral signature characteristics not found in auto-fluorescence and similar emission mechanisms. The mechanisms of reflection and emission that the present invention addresses are narrow band phenomena. These phenomena are spectrally narrow in comparison to auto fluorescence and tissue absorption mechanisms found in the art. Spectral signatures associated with cancerous tissue may have subtle features which are hidden in narrow bands. To detect these features, one must employ systems having high spectral resolution. Hyperspectral imaging systems can have sufficient resolution to detect such subtle features.

Not only is it valuable to detect the presence of cancer, but it is also important to locate in detail the extent of the spread of cancerous tissue. A map showing which tissue is cancerous and which is healthy can aid in the accurate removal of tumors. Some systems employ single point detection and do not show the extents of the tissue region which has been affected. Therefore, it is the combination of spatial resolution and high spectral resolution of hyperspectral imaging systems which affords great utility to the use of these systems for diagnosis of tissue for cancer.

In addition, the techniques used do not require introduction of harmful agents into the tissue nor the supporting procedures used therewith, the instant invention is entirely non-invasive and works in real-time.

Of particular interest is the novel communication of a three dimensional optical imaging system with the particular task at hand. Specifically, a hyperspectral imaging system arranged for use to detect and diagnose cancers of the epidermis. Since a hyperspectral imaging system necessarily gathers data in three dimensions, two space and one spectral, the optical arrangement is atypical. Specifically, a plurality of line images are formed sequentially. For each line image at a single tissue, the line image is dispersed into its spectral components along one spatial dimension. The spectral content of the line image is then measured with high resolution in many narrow bands. Successive spectra of line images are similarly recorded until an image having two spatial dimensions and a spectral dimension is formed.

It is a primary object of the invention to provide new systems and methods for the diagnosis of tissue conditions.

It is an object of the invention to provide novel systems and methods for the diagnosis of tissue with respect to detecting cancerous tissue by employing hyper-spectral imaging techniques.

It is a further object of the invention to provide systems and methods for detecting and analyzing cancerous tissues by comparing a plurality of spectrum resolved images of suspect tissue.

It is still further an object of the invention to provide an optical arrangement suitable for collecting hyperspectral optical information from tissues for the analysis relating to diagnosis and detection of cancer.

It is further an object of the present invention to provide a plurality of chromatic and spatially resolved images of tissue for diagnosis.

A better understanding can be had with reference to Detailed Descriptions of some Preferred Embodiments and with reference to the appended drawings. These embodiments represent particular ways to realize the invention and are not inclusive of all ways possible. Therefore, there may exist embodiments which do not deviate from the spirit and scope of this disclosure as set forth by the claims, but do not appear here as specific examples. It will be appreciated that a great plurality of alternate versions are possible.

BRIEF DESCRIPTION OF THE DRAWINGS

Certain features, aspects, and advantages of the present invention will become better understood with regard to the following description, appended claims and drawings where:

FIG. 5 is a plot of the result of subtracting two spectra;

FIG. 6 is a map of the areas where test matter is detected;

FIG. 7 is an example of a spectrum having many fine features of the type not found in broad band systems.

DETAILED DESCRIPTION OF SOME PREFERRED EMBODIMENTS

Figure 1:
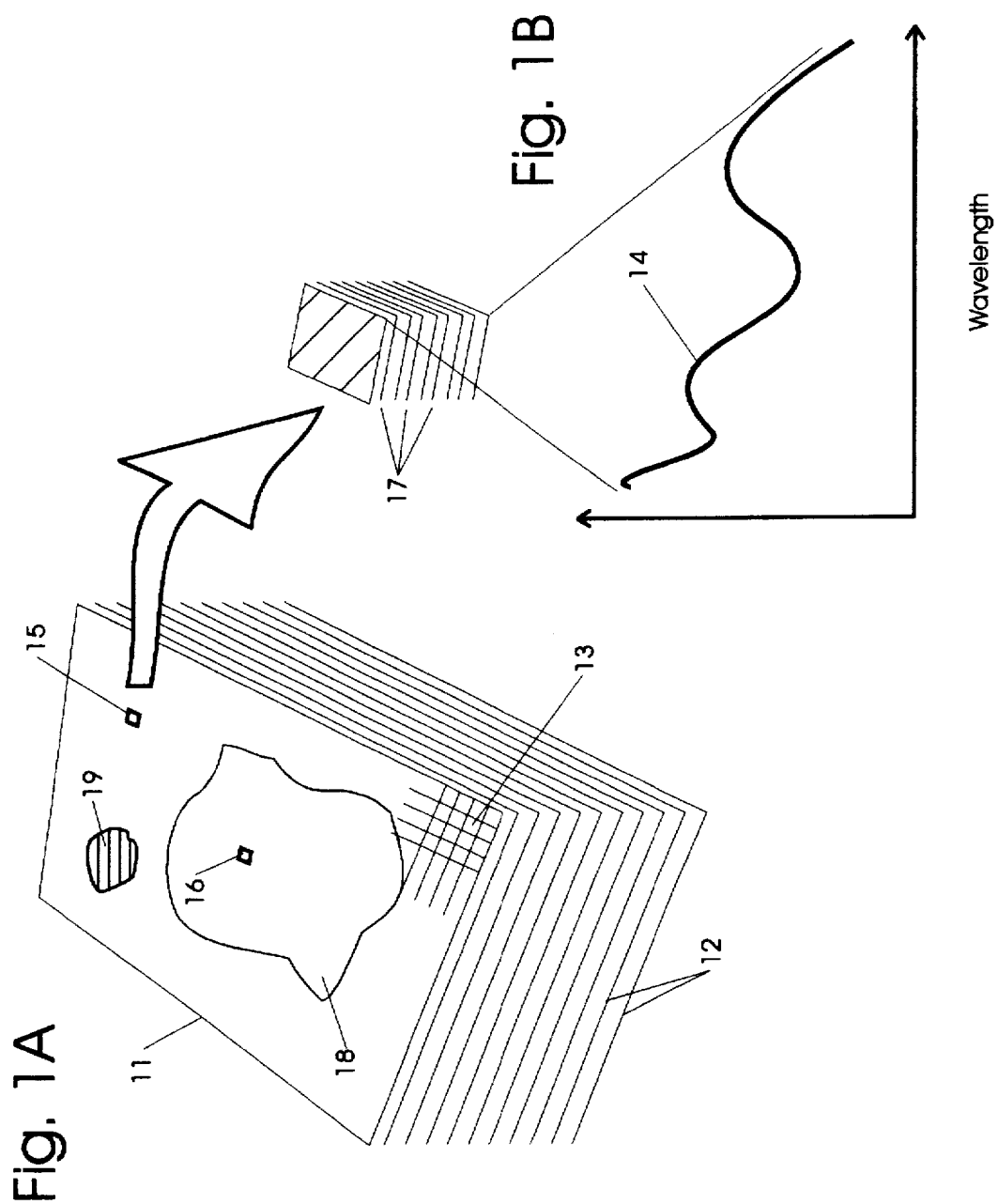
FIG. 1 is a graphic which illustrates the multi-dimensional nature of a hyperspectral image.

A greater appreciation of the invention may be had by considering the drawing figures and following detailed description.

In a first preferred embodiment, an area of interest 11 contains tissue to be diagnosed. This tissue may be skin tissue having abnormal coloration or other indicator which renders the tissue suspect. In the example illustrated in FIG. 1, the area of interest has within it three regions, a first region indicated by 18, a second region indicated by 19, and the balance of the area of interest. The entire tissue area can be divided into an array 13 of pixels in two dimensions covering the entire area. Single pixels can be found in each of the regions. Pixel 16 is in the region 18 and pixel 15 is in another region. When a single pixel is addressed by the system, it can be sampled on some interval for its spectral content. Each spectral band 17 has associated therewith some intensity level for that single pixel. Each other pixel may have different spectral content. It is of great interest to the present invention to analyze the point-by-point spectra over a tissue area of interest.

Figure 2:
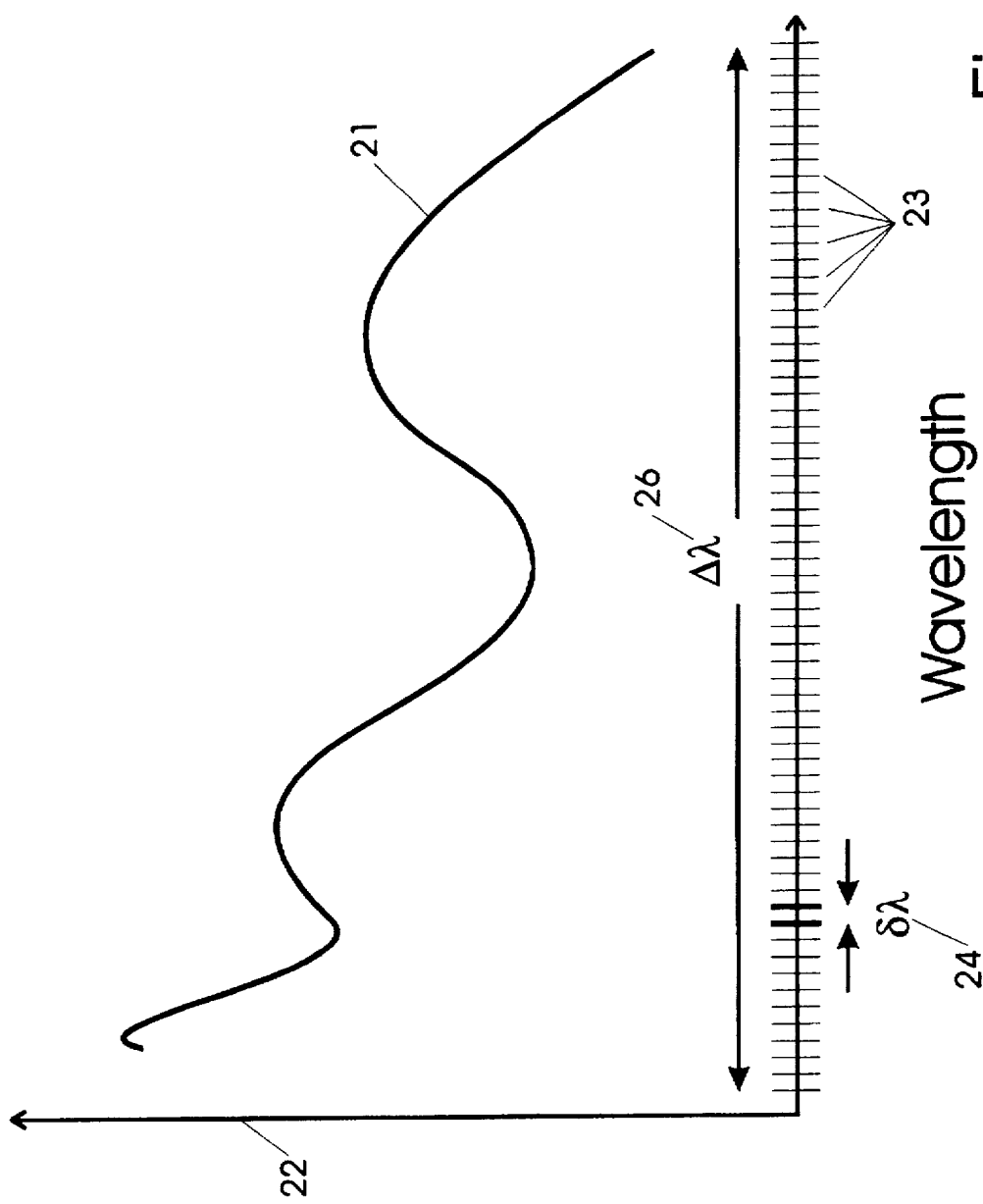
FIG. 2 is a plot of wavelength versus intensity for a plurality of spectral bands.

FIG. 2 shows a plot 21 of the spectrum for the single pixel 15 over some range of wavelengths 26. This range may extend into or beyond the UV and IR regions of the spectrum. The vertical axis of this plot indicates intensity and the horizontal axis indicates varying wavelength. A single spectral band 24 is of some finite size restricted by the discretization of the detector elements. The bandwidth of a single spectral channel is narrow in comparison to the bandwidth associated with phenomena like autofluorescence. For preferred embodiments, it may be convenient for the spectral range to be comprised of 64 wavelength channels 23. For each pixel of the area of interest, which there may be many, there is a spectrum corresponding thereto.

The spectrum 21 shown in FIG. 2 may be that which is associated with normal healthy tissue when illuminated with a white light source or a special illumination source having some preferred spectral content. When cancer or some other matter of interest is present, that matter may interact with the light from the illumination source. There are well known absorption and emission mechanisms which could alter the spectrum which is reflected from the tissue being tested. If cancer is present in the test sample, the measured spectrum may contain spectral components in addition to the components associated with healthy tissue. The additional components being attributable to the interaction of the light with the cancerous tissue.

Figure 3:
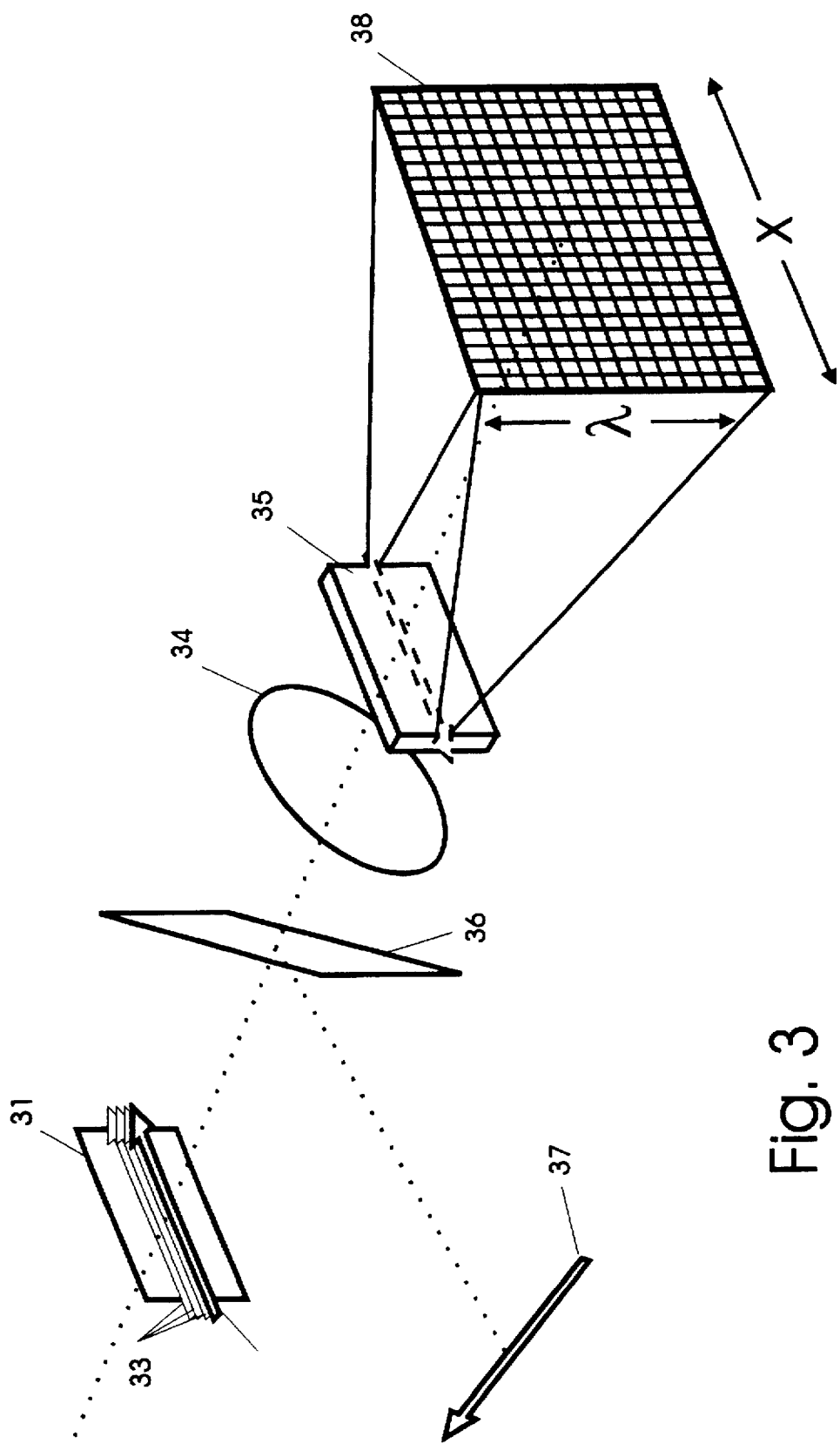
FIG. 3 is an optical set-up which may be used to obtain a hyperspectral image.

In order to gather data as described, one may employ an optical system of FIG. 3. An image plane 31 is addressed with a plurality of line regions 33 over time. A single line is scanned sequentially along a spatial dimension. A light source 37 can illuminate a line region via a beam combiner 36. The light source includes beam forming optics for focusing light into a ribbon shaped beam oriented substantially orthogonal to its direction of propagation having a cross section with a high aspect ratio, its width being substantially smaller than its breadth, and optionally including a chromatic filter, the beam forming optics being in optical communication with the tissue to be diagnosed. The light source further includes a scanning mechanism for projecting the ribbon shaped beam onto a sample of tissue whereby the light illuminates a first portion of the tissue sample at a single time. The scanning mechanism is further operable for projecting the ribbon beam onto a second portion of the tissue sample after the first portion has been sufficiently illuminated and for projecting the ribbon beam onto other portions of the tissue sample in sucession thereby covering the entire tissue sample. The imaging optic 34 operates to image the line in the plane of a detector 38. Dispersing element 35 breaks the line image into two dimensional detector space. One detector dimension represents a space dimension in the object domain and the other detector space dimension represents an object spectral dimension. The detector may include a comparator electrically connected to the detector and operable for receiving a signal from the detector and comparing the signal to a reference signal and an indicator in communication with and responsive to the comparator and operable for indicating coincidence and lack of coincidence between the reference signal and the signal from the detector.

Figure 4:
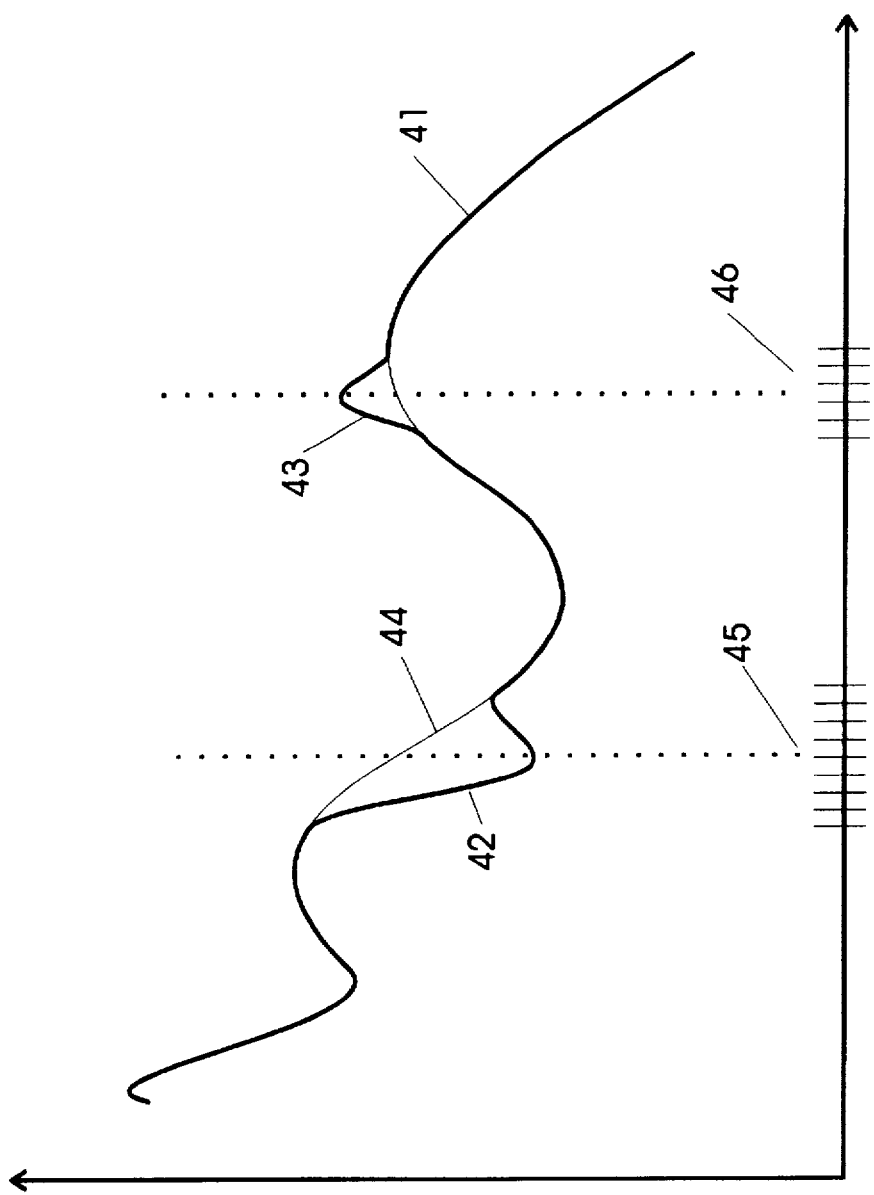
FIG. 4 is a spectrum similar to the spectrum of FIG. 2 which shows effects from the presence of certain matter.

For the sake of argument, an example of absorption spectrum which illustrates spectral response to the presence of certain matter has been devised. The spectrum from a single pixel is shown as 41 in FIG. 4. In a particular region of the spectrum 41, eight spectral channels 45 show a reduced intensity for each of those channels. This could be expected when matter is present which is highly absorptive for those wavelengths. It is also possible that certain energetic photons from the source stimulate emission mechanisms which yields an increase in intensity at particular regions of the spectrum. The five channels 46 show an increase in intensity in comparison to the spectrum associated with the healthy tissue of FIG. 2 shown in the figure as the thin line 44.

Not all healthy tissue can be expected to have the same spectrum. This can be illustrated by the common mole. It is clear that a mole, which is dark in color, would have a reflection spectrum which is quite different than the spectrum of other regions of skin tissue. In addition, the skin of a first person can have spectra quite different in comparison to a second person. People of different races are likely to possess tissue which responds differently to light incident on that tissue. For this reason, it may be necessary to compare the spectrum from a tissue site known to be healthy to the spectrum of a site of the same person suspected to be cancerous. With this in mind, the spectra of FIG. 4 are considered again here. If we perform a point-by-point subtraction routine on the two spectra plots 44 and 42 to yield a spectra difference signal, it may be possible to isolate spectral feature activity due to the interaction of light with the test matter, for example cancerous matter. If the difference spectra signal is compared to a reference signal, a match could indicate the presence of the test matter. The plot in FIG. 5 shows the result of a subtraction operation on the two spectra of FIG. 4; a spectra difference signal. Regions 51 and 52 may indicate activity due to the interaction of light with cancerous tissue. Since the difference signal is independent of spectral features associated with race or normal skin variations, it is possible to isolate the spectral activity associated with the matter being tested. It may also be necessary to formulate a library of reference signals. The reference signals may be particular to race or other factors which are found to affect these spectral difference signals.

One may now consider "what happens when a single patient has healthy tissues having varying spectra within a test area?" For example, the test area 11 of FIG. 1 may be comprised of: healthy tissue 15, a mole 18 having both a region of healthy tissue and a region of cancerous tissue. This condition may be accounted for by considering the following scheme. The spectrum of one pixel can be subtracted from the spectrum of another nearby pixel. If the two pixels straddle a region of change from one type of healthy tissue to another, then the subtraction will yield something which is independent of the "signature" reference. Two pixel spectra can be subtracted from each other and then compared to a reference to determine if there exists correspondence. If such correspondence is detected, the change may be attributable to cancer and not to a normal transition from one type of healthy tissue to another. When comparing the spectrum difference signal to the reference, one can rely on sophisticated mathematical techniques known as correlation.

FIG. 6 shows a broken line 64 which was found by comparing a difference spectra to a reference signal. The test indicates a positive result along a closed path. It may be concluded that the shaded region 67 is the area having cancerous tissue. Note that the region shown in FIG. 6 enclosed by the line 63, may not necessarily define the cancerous region. That line may simply represent a mole which is visible to the eye. In fact, the area 66 within the mole may be healthy tissue and the region 67 within the mole may be cancerous. Regions 62 and 65 indicate regions having healthy tissue.

The preceding examples were contrived for clarity. It is not likely to be the case that a single broad absorption band and a single broad emission band exist in the spectra of cancerous tissues. In fact, the spectral features associated with most materials are extremely complex with many absorption bands and emission bands of varying intensity. The spectrum of FIG. 7 is an example of a spectrum which has many narrow band features. It is precisely this kind of data which can be accurately appraised via a hyperspectral imaging system. In some preferred embodiments of the invention, the measured spectrum can be comprised of 64 spectral channels. For this reason, it is not possible to look with wavelength tuned detectors at a few spectral bands.

One may find in the art that if a well behaved agent is attached to the target tissue that such simple technique may be effective. However when using advanced processing techniques such as spectral differencing and correlation, the number of spectral channels is necessarily large in order to enable those methods.

Although some known cancer detection schemes employ multiple spectral channels to measure for certain optical activity, these systems have heretofore been reliant on strong broadband effects. To stimulate such activity, it is sometimes required that an agent be introduced into the system. The present invention includes a completely non-invasive technique which relies on detailed spectral analysis to detect cancerous tissue. A plurality of narrow band measurements can contain subtle spectral features indicating the presence of cancerous tissue.

In accordance with each of the preferred embodiments of the invention, there is provided an apparatus for and method of diagnosing tissue for cancer via hyperspectral imaging. It will be appreciated that each of the embodiments described include either an apparatus or method and that the apparatus or method of one preferred embodiment may be different than the apparatus or method of another embodiment. Although the present invention has been described in considerable detail with clear and concise language and with reference to certain preferred versions thereof including the best mode anticipated by the inventor, other versions are possible. Therefore, the spirit and scope of the appended claims should not be limited by the description of the preferred versions contained therein.

We claim:

1. An apparatus for diagnosis of tissue, the apparatus being optically coupled to the tissue being diagnosed, comprising:
   a) a light source;
   b) an imaging optic;
   c) a dispersion optic;
   d) a detector;
   e) a comparator; and
   f) an indicator,
   said light source operable for converting electric energy to photon energy, the photon energy being coupled to tissue being diagnosed;
   said imaging optic being disposed between the tissue and said detector in a manner which satisfies the imaging condition thereby forming an image on said detector;
   said dispersion optic disposed between the tissue and said detector for dispersing light into a hyperspectral image;
   said comparator being in electronic communication with said detector operable for receiving a signal from said detector and comparing it to a reference signal; and
   said indicator being in communication with and responsive to said comparator operable for indicating coincidence and lack of coincidence between the reference and signal from said detector.

2. An apparatus of claim 1:
   said light source further comprising:
   a) beam forming optics; and
   b) a scanning mechanism.
   said beam forming optics operable for focusing light into a ribbon shaped beam oriented substantially orthogonal to its direction of propagation having a cross section with high aspect ratio, its width being substantially smaller than its breadth, and optionally including a chromatic filter, said beam forming optics being in optical communication with the tissue to be diagnosed by way of,
   said scanning mechanism operable for projecting the ribbon shaped beam onto a sample of tissue whereby the light illuminates a first portion of the tissue sample at a single time, further operable for projecting the ribbon beam onto a second portion of the tissue sample after the first portion has been sufficiently illuminated, and further operable for projecting the ribbon beam onto other portions of the tissue sample in succession thereby covering the entire tissue sample,
   said dispersion optic further comprising:
   a) a dispersion direction; and
   b) a neutral direction,
   said dispersion direction oriented orthogonal to the direction of the ribbon shaped beam thereby dispersing that beam such that the width is spread into a plurality of spectral bands;
   said neutral direction not appreciably affecting the ribbon shaped beam in any way thereby allowing the beam to pass therethrough,
   said detector further comprising:
   an array of detector elements regularly arranged along two directions, a first direction corresponding to the direction of the ribbon shaped beam and a second direction corresponding to the dispersion direction, each detector element operable for detection of the intensity of light incident thereon,
   said comparator further comprising:
   a) a reference signal; and
   b) comparison means,
   said reference signal being associated with known spectral features which correspond to optical activity in a particular matter;
   said comparison means operable for comparing said reference signal to the spectral content associated with each detector element.

3. A method for diagnosis of tissue comprising the steps:
   a) illuminating a tissue sample;
   b) forming a hyperspectrally resolved image of the tissue sample;
   c) comparing the hyperspectrally resolved image with a reference; and
   d) indicating regions of coincidence and regions of non-coincidence with respect to the hyperspectrally resolved image and the reference,
   said hyperspectrally resolved image being comprised of a plurality of spectral bands, each spectral band being adjacent to another forming a continuous set, each spectral band having a bandwidth less than about 10 nanometers.

4. The method of claim 3, the steps being further defined as:
   a) illuminating a surface of the tissue sample by sequential application of a ribbon illumination beam;
   b) forming a hyperspectral image of the tissue sample by recording a spectrum for each of a plurality of points along each illumination line;
   c) comparing point-by-point the spectra of the hyperspectral image with a reference spectrum to determine coincidence therebetween for each point; and
   d) indicating regions where coincidence occurs thereby indicating the presence of matter associated with the reference and regions where coincidence does not occur thereby indicating absence of the matter associated with the reference.

5. The method of claim 3 where:

illuminating the surface of the tissue sample further comprises exciting a light source and forming a linear beam of light, projecting the linear beam onto a first line of the tissue sample surface, projecting the beam onto a second line of the tissue sample surface, projecting the beam onto a series of lines sequentially until the entire surface of the tissue sample has been illuminated;

forming a hyperspectral image of the tissue sample further comprises measuring the spectral content of reflected light from each of a plurality of sub-area elements which cover a two dimensional area of the tissue sample;

comparing the spectrum of each sub-area element to a reference signal associated with a cancerous tissue spectral signal to determine if a coincidence occurs; and indicating regions where coincidence occurs thereby indicating the presence of cancer and regions where coincidence does not occur thereby indicating absence of cancer.

* * * * *